United States Patent
Farin

(10) Patent No.: US 11,109,908 B2
(45) Date of Patent: Sep. 7, 2021

(54) RF SURGICAL RESECTION SNARE FOR FLEXIBLE ENDOSCOPY

(71) Applicants: Günter Farin, Tübingen (DE); ENDOX FEINWERKTECHNIK GMBH, Bad Urach (DE)

(72) Inventor: Günter Farin, Tübingen (DE)

(*) Notice: Subject to any disclaimer, the term of this patent is extended or adjusted under 35 U.S.C. 154(b) by 179 days.

(21) Appl. No.: 15/320,890

(22) PCT Filed: Jun. 25, 2015

(86) PCT No.: PCT/EP2015/064387
§ 371 (c)(1),
(2) Date: May 24, 2017

(87) PCT Pub. No.: WO2015/197765
PCT Pub. Date: Dec. 30, 2015

(65) Prior Publication Data
US 2018/0263687 A1   Sep. 20, 2018

(30) Foreign Application Priority Data
Jun. 25, 2014   (EP) .................................... 14173888

(51) Int. Cl.
*A61B 18/14* (2006.01)
*A61B 18/00* (2006.01)

(52) U.S. Cl.
CPC ...... *A61B 18/1492* (2013.01); *A61B 2018/00077* (2013.01); *A61B 2018/00083* (2013.01);
(Continued)

(58) Field of Classification Search
CPC ...... A61B 2018/141; A61B 2018/1407; A61B 17/221; A61B 17/32056;
(Continued)

(56) References Cited

U.S. PATENT DOCUMENTS 4,493,320 A * 1/1985 Treat ................ A61B 18/14
606/47
5,078,716 A * 1/1992 Doll ................. A61B 18/14
606/47
(Continued)

FOREIGN PATENT DOCUMENTS

CN   103281980 A   9/2013
DE   7111578 A1   8/1971
(Continued)

OTHER PUBLICATIONS

Office Action issued in related Chinese Patent Application CN201580029367.9, dated Jul. 30, 2018.
(Continued)

*Primary Examiner* — Eun Hwa Kim
*Assistant Examiner* — Adam Z Minchella
(74) *Attorney, Agent, or Firm* — Yakov Sidorin; Quarles & Brady LLP

(57) ABSTRACT

A polypectomy snare comprising two snare parts has a snare part that is completely electrically insulated and another snare part that is not electrically insulated in at least one distal portion thereof. The snare furthermore has at least one electrically insulated, HF surgically inactive skid at its distal end.

13 Claims, 3 Drawing Sheets

(52) U.S. Cl.
CPC ............... *A61B 2018/00494* (2013.01); *A61B 2018/00601* (2013.01); *A61B 2018/00982* (2013.01); *A61B 2018/141* (2013.01); *A61B 2018/1465* (2013.01); *A61B 2018/1475* (2013.01); *A61B 2018/1497* (2013.01)

(58) Field of Classification Search
CPC .... A61B 2017/00358; A61B 2018/144; A61B 18/1492; A61B 2018/00077; A61B 2018/00083; A61B 2018/00494; A61B 2018/00601; A61B 2018/00982; A61B 2018/1465; A61B 2018/1475; A61B 2018/1497
See application file for complete search history.

(56) References Cited

U.S. PATENT DOCUMENTS

| | | | |
|---|---|---|---|
| 5,555,883 A * | 9/1996 | Avitall | A61B 5/6856 600/374 |
| 5,846,248 A * | 12/1998 | Chu | A61B 17/221 606/114 |
| 6,022,362 A | 2/2000 | Lee et al. | |
| 7,655,013 B2 | 2/2010 | Bieneman | |
| 2008/0009883 A1 * | 1/2008 | Bieneman | A61B 17/221 606/113 |
| 2009/0182324 A1 * | 7/2009 | Kurtulus | A61B 18/14 606/37 |
| 2010/0036375 A1 * | 2/2010 | Regadas | A61B 17/32056 606/39 |
| 2011/0282335 A1 * | 11/2011 | Jia | A61B 18/082 606/27 |
| 2012/0172864 A1 * | 7/2012 | Farin | A61B 18/14 606/33 |
| 2012/0283723 A1 * | 11/2012 | Jenkins | A61B 18/14 606/41 |
| 2014/0046320 A1 * | 2/2014 | Kappel | A61B 17/00234 606/40 |
| 2015/0094719 A1 * | 4/2015 | Batchelor | A61B 18/14 606/50 |
| 2015/0105789 A1 * | 4/2015 | Raybin | A61B 17/32056 606/113 |
| 2018/0263687 A1 | 9/2018 | Farin | |

FOREIGN PATENT DOCUMENTS

| | | | |
|---|---|---|---|
| DE | 10028413 A1 | 9/2001 | |
| DE | 10 2009 036158 | 2/2011 | |
| EP | 1 180 349 | 2/2002 | |
| EP | 1180349 A1 * | 2/2002 | ......... A61B 18/1482 |
| WO | 2011012616 A2 | 2/2011 | |
| WO | 2013064576 A1 | 5/2013 | |

OTHER PUBLICATIONS

The International Search Report dated Sep. 14, 2015 for International Application No. PCT/EP2015/064387.

Office Action issued in related Chinese Patent Application CN201580029367.9, dated Feb. 19, 2019.

* cited by examiner

RF SURGICAL RESECTION SNARE FOR FLEXIBLE ENDOSCOPY

CROSS-REFERENCE TO RELATED APPLICATIONS

This application is a national phase from the International Patent Application PCT/EP2015/064387 filed on Jun. 25, 2015, which claims priority from European Patent Application EP 14173888.0 filed on Jun. 25, 2014. The disclosure of each of the above-mentioned patent documents is incorporated herein by reference.

TECHNICAL FIELD

The invention relates to high-frequency surgical (HF-surgical) resection snares for instruments or as part of instruments for endoscopically controlled removal of polyp-like or flat-growing pathological mucosa areals (so-called lesions) of the gastrointestinal tract. These instruments are named, inter alia, polypectomy or —pars pro toto —polyp snares.

PRIOR ART

One of the first of these tools was described in 1971, in the German utility model No. 71115781. Today, as then, these instruments essentially consist of a flexible 2m long catheter made from a plastic material, a metallic manipulation wire movable in the catheter, an HF-surgical metallic resection snare at one—the so-called distal—end of the manipulation wire, and a manipulation handle at the other—the so-called proximal—end of the manipulation wire. The catheter with the resection snare of these instruments has been used for more than 40 years through so-called instrumented or working channels of flexible endoscopes, to HF-surgically remove lesions of the mucosa of the gastrointestinal tract, as prophylactic against gastrointestinal cancer.

While until about 20 years ago only relatively small lesions (<2 cm) have been removed with these instruments, it is the current trend today to remove even large lesions (>2 cm) by means of these instruments. However, this trend is accompanied by some problems. The larger the lesion, the greater is the likelihood of manifested carcinoma in this lesion. Therefore, oncologists demand that especially large lesions be removed in sano, i.e. in the adjacent healthy tissue.

In order to be able to surely check pathohistologically if the removal of the lesion actually took place in sano and whether carcinoma (cancer tissue) is already present in the removed lesions, and if so, whether this cancer has already infiltrated into lymphatic and/or arterial vessels, and thus already bears the risk of metastases in other organs, pathologists demand the removal of the lesion en bloc, i.e. in a single piece and including the submucosa located below the lesion, at least the upper third of the submucosa (the so-called sm1). To meet this requirement of the pathologists, it is appropriate to inject, for example, physiological NaCl solution into the submucosa, such that as a result of absorption of NaCl solution, the submucosa not only swells, thus becoming thicker, but also the specific electrical conductivity of the submucosa increases. In consideration for the above-mentioned demands of oncologists, lesions have to be removed with a circumferential safety distance of 5 mm, in case of a 3 cm lesion for example, a mucosal area of 4 cm diameter has to be HF-surgically removed en bloc.

The HF-surgical en bloc removal of large lesions (>2 cm) with HF-surgical snares or polypectomy snares is problematic in so far as for an HF-surgical cut during the so-called initial cut phase (that is the time between the activation of the HF-power generator and the electric arc between polypectomy snare and tissue which is necessary for HF-surgical cutting of tissues), an HF power of at least 0.5 $A_{eff}$ per cm snare length is required, such that the cut may be generated with a delay (the so-called initial cut delay), as small as possible. If the initial cut delay is too long, there is a risk that the organ wall below the lesion is thermally damaged, and postoperatively, a so-called post polypectomy perforation of the organ wall may occur. Since HF generators available in endoscopy perform an HF power with a maximum of only 1.5 to 2.0 $A_{eff}$, only lesions at an effective snare length of 3 to 4 cm, which corresponds to a diameter of about 1 to 1, 5 cm, can be sufficiently removed without delay.

A further problem of polypectomy snares available so far is that they can cut in all directions, especially towards the organ wall. In order to avoid a cut towards the organ wall or even through the organ wall, these polypectomy snares may not be pressed against the organ wall during the activation of the HF power generator, and the incision must be performed away from the organ wall. This is particularly problematic with the HF-surgical removal of large sessile polyps and large flat lesions, in so far as an incision plane parallel to the organ wall or to the muscularis *propria* below the lesion is not possible. As a consequence, in particular large lesions cannot completely be removed en bloc. Therefore, large lesions are removed by means of the so far available polypectomy snares in several smaller pieces (piece meal technique) or with the method developed in Japan, which is called Endoscopic Submucosal Dissection (ESD). The piece meal technique does not meet the above-mentioned requirements of the pathologists. The ESD is difficult and time consuming in use.

In the German application publication DE 100 28 413 A1, electrosurgical instruments each with an electrode, inter alia also snare electrodes, with a so-called electrode core and an insulation coating partially covering the electrode core are disclosed. Here, the free electrode surface of the electrode core is symmetrically reduced at the snare tip by an insulation coating with a plurality of openings or by an insulation coating enclosing the electrode core only in a circular segment.

In this way, the amperage required for cutting is to be reduced. With these snare electrodes, the above-mentioned problem of a too long initial cut delay can be eliminated. However, the manufacturing of these snare electrodes is very complicated due to the segmentation of the coating.

Moreover, these snare electrodes must not be pressed against the organ wall during activation of the HF power generator and in particular during the HF-surgical incision, because these snare electrodes can cut also towards the organ wall.

A further problem with application of all so far available polypectomy snares is that neither the endoscopist nor his assistant (for example an endoscopy nurse) can observe or control visually, especially during the HF-surgical incision, whether, and if so, how quickly the HF-surgical resection snare closes. Due to the more or less large elasticity of the long catheter on the one hand and of the manipulation wire on the other hand, as well as due to the considerable friction between catheter and manipulating wire, and also because of the large axial dead travel (hysteresis) between manipulation handle and resection snare in polypectonomes available so far, reliable control of closing the snare at the manipulation handle is usually not possible. However, control of closing the snare as well as of the speed of the incision is very important regarding cutting quality and especially regarding a vascular occlusion synchronous to the cutting.

SUMMARY OF THE INVENTION

It is an object of the invention to develop HF-surgical resection snares for instruments or as part of instruments for endoscopically controlled removal of polyp-like or flat-growing pathological mucosa areas (so-called lesions) of the gastrointestinal tract, in which the above-mentioned problems do not occur.

Such resection snares are also called snares hereinafter.

In particular, it is an object of the invention to develop such resection snares, which have an initial cutting delay as short as possible in use, and which can nevertheless be manufactured as simply as possible.

It is furthermore an object of the invention to develop such resection snares, that may be pressed against the organ wall during activation of the HF-generator as well as during the HF-surgical incision, without cutting into or even through the organ wall.

It is furthermore an object of the invention to develop such resection snares with which the endoscopist and/or the assistant (for example an endoscopy nurse) can also visually control or observe the opening and closing of the snare—even when the snare being looped around a lesion is not visible, which is crucial especially during the incision.

The object of the invention is achieved by an HF-surgical resection snare according to independent claim 1. Further embodiments are described in the dependent claims.

The HF-surgical resection snare comprises a first snare part and a second snare part. The two snare parts comprise a wire, preferably a solid wire, particularly preferably made of steel or nitinol, and they each have a proximal end and a distal end. They form a snare tip with their distal ends. Optionally two snare parts may be connected at their distal ends to form a snare tip. Alternatively, the snare can also be made of one piece, wherein the two snare parts consist of one part.

At their proximal ends, the two snare parts are connected to a manipulation wire, by means of which they can be drawn into and/or pushed out of a catheter.

At least one snare part is electrically insulated in a proximal region and is not electrically insulated in a distal region (towards the snare tip). Optionally, one snare part is completely electrically insulated. In an alternative embodiment, a maximum of three, more preferably two non-insulated regions are provided. Measurements with various HF-surgical generators have furthermore shown that snares according to the invention show substantially improved incision properties. Thereby, the shortened insulated part when compared to the total snare length leads to a sufficiently high HF power density even in HF surgery generators with low output current, that ensures safe incision.

Furthermore, the snare comprises at least one skid example at its distal end. The skid is electrically insulated and thus HF-surgically inactive. It serves to support the snare against the tissue, preventing the snare end to penetrate into the tissue. Thus, the risk of the undesired incising of the snare into the tissue can be substantially reduced.

Optionally, there is a protection at least at one end of the skid. This may be a rounding or a kind of a thickening, such as for example, a spherically formed end.

Such a protection may, for example, avoid damaging of an instrumentation channel of an endoscope when the snare is pushed through. In addition, piercing of the tissue can be avoided when using the resection snare. In another embodiment, at least one end of a skid is formed as a tip, such that it can be inserted into the tissue, for example for fixation in the tissue.

Advantageously, the end of at least one skid lies behind the non-insulated region when seen from snare center or from the catheter end, and thus enables mechanical support behind this area. The centroid of the area enclosed by the snare can be used as snare center, for example.

Preferably, the length of a skid is in the range of 5 mm to 40 mm, more preferably from 10 mm to 40 mm, and most preferably from 10 mm to 15 mm.

Preferred embodiments of the skids are at least 1 mm or at least 2 mm wide and have a length of at least 2 mm or at least 3 mm or at least 5 mm. Preferably, at least one skid has a circumference of at least 5 mm or at least 8 mm. Furthermore, at least one skid preferably has a sliding surface of at least 2 mm$^2$ or at least 5 mm$^2$.

Preferably, the snare parts comprise resilient, metallic round and/or flat wire. Alternatively, they can also comprise preferably resilient metallic braid.

Advantageously, the non-insulated snare part can be provided with an anti-slip coating or with small, preferably centripetally aligned teeth, which facilitates the application on or around slippery lesions.

Advantageously, all above-mentioned inventive snares can be equipped with a manipulating handle according to WO 2013/064576.

DESCRIPTION OF THE DRAWINGS

In FIG. 1, an inventive HF-surgical resection snare 1 for flexible endoscopy is shown. It comprises a first snare part 2 and a second snare part 3. These snare parts comprise preferably resilient, metallic round and/or flat wire. Alternatively, they may also comprise metallic braid. Each of the snare parts has a proximal end 11 and a distal end 10. The proximal ends of the snare parts together form the proximal end 11 of the snare. They are mechanically and electrically conductive connected with at least one manipulation wire 8, for example by a connecting element 12, or they are formed as a manipulation wire. For example, at least one of the snare parts may be considerably extended at its proximal side, such that the extension serves as a manipulation wire. Furthermore, the both snare parts form a distal snare end 10 with a snare tip 7. The snare tip is optional, but is usually required to design a snare being retractable into a catheter. Both snare parts may also be formed by a continuous wire. Furthermore, the two snare parts are preformed, such that they together form a resiliently deformable HF-surgical snare 1. With such a snare, a polyp-shaped or flat-growing pathological tissue area can be wrapped and removed from an organ wall with or without suitable preparation, for example sub-mucosal injections and circumferential circumcision.

Figure 1:
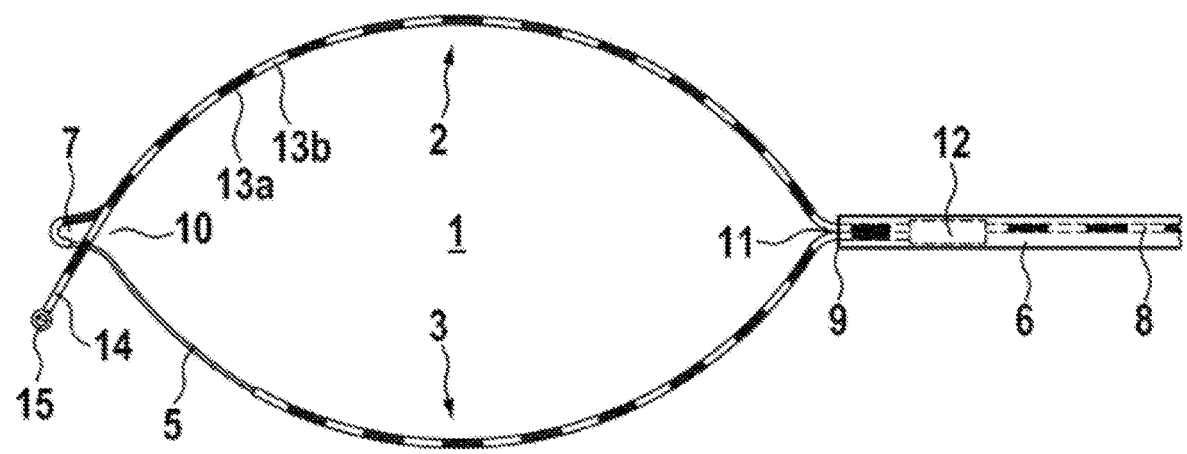
FIG. 1 shows a snare according to the invention.

Furthermore, the first snare part 2 is preferably completely electrically insulated. The second snare part 3 is electrically insulated in a proximal region and electrically non-insulated in a distal region 5.

For better evaluation of cutting progress, markers 13a, 13b are provided on the snare parts and/or the manipulation wire. Preferably, they show a significant color contrast against each other. In this way, movement with respect to the distal end 9 of the catheter can be well observed.

A skid 14 starts from the first snare part 2. It may as well start from the second snare part 3. However, the embodiment illustrated here is particularly advantageous, as the end of the skid lies behind the non-insulated region 5 when seen from snare center, and thus allows a mechanical support just behind this region.

The centroid of the region enclosed by the snare can be used as snare center, for example. In the embodiment illustrated here, the skid 14 intersects the non-insulated region 5. Preferably, there is a protection 15 located at the end of the skid. The snare gets closer upon further contracting it, such that the first snare part and the second snare part approach each other. Thus, in this embodiment, the skid 14 pivots in a direction parallel to the longitudinal axis of the catheter. In the illustration according to FIG. 1, this corresponds to an upwards pivoting.

When the snare is completely drawn into the catheter, the skid 14 lies above the catheter tip 7.

Figure 2:
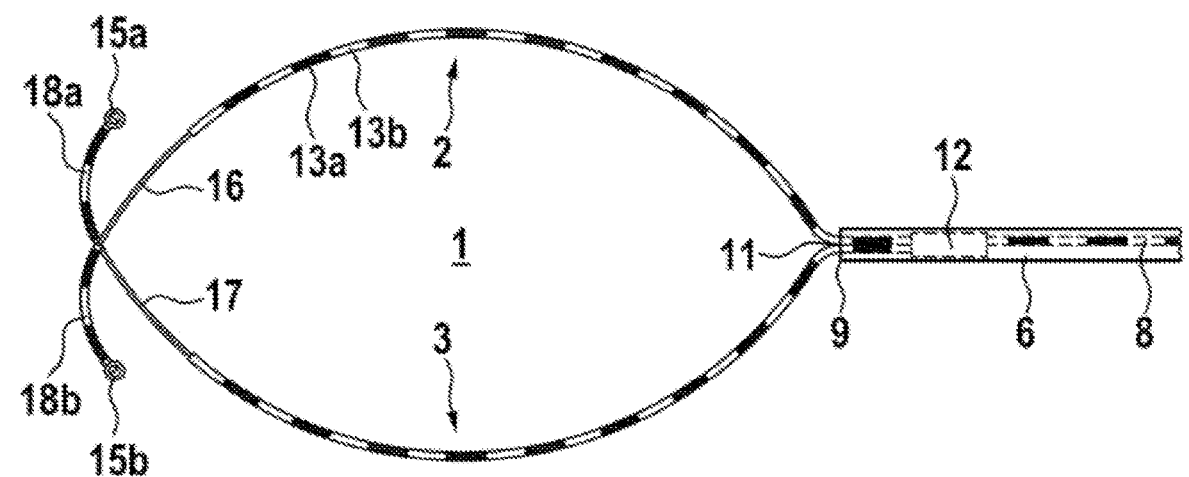
FIG. 2 shows a snare with two skids.

In FIG. 2, a further embodiment with two skids 18a, 18b is shown. These skids have a protection 15a, 15b at their respective ends. In this exemplary embodiment, the first snare part 2 has a first non-insulated region 16 and the second snare part 3 has a second non-insulated region 17.

Basically, in line with this invention, one or more non-insulated regions can be combined with the various skids illustrated herein. However, it is particularly preferred to use two skids, when two non-insulated snare parts are present, as shown in FIG. 2.

Figure 3:
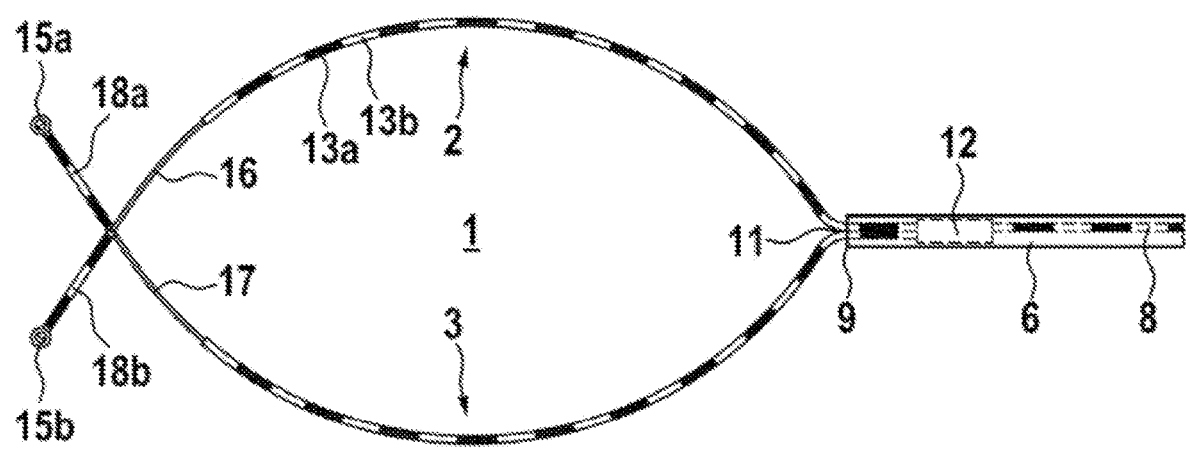
FIG. 3 shows a snare with straight skids.

In FIG. 3, a further embodiment is shown, in which the skids are formed straight.

Figure 4:
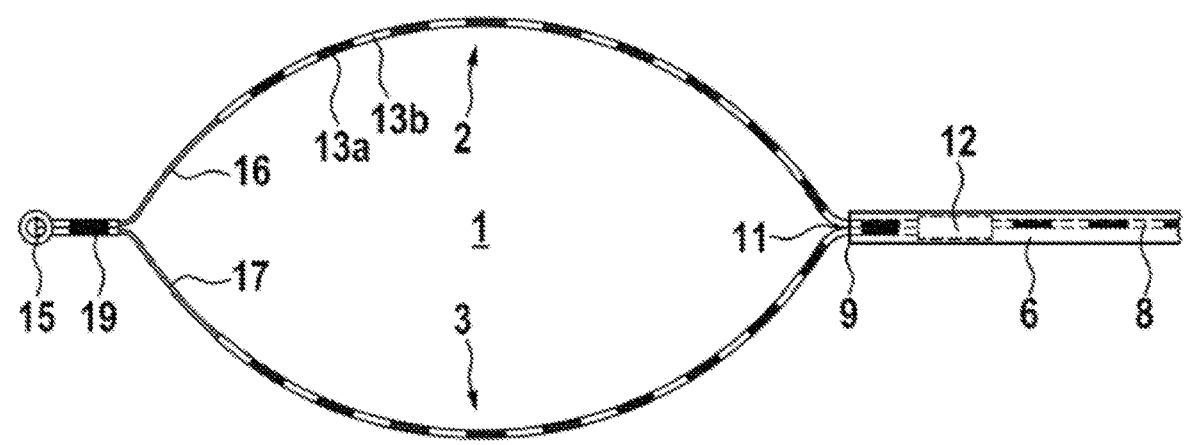
FIG. 4 shows a snare with a symmetrically arranged skid.

In FIG. 4, a single symmetrically arranged skid 19 is shown.

Figure 5:
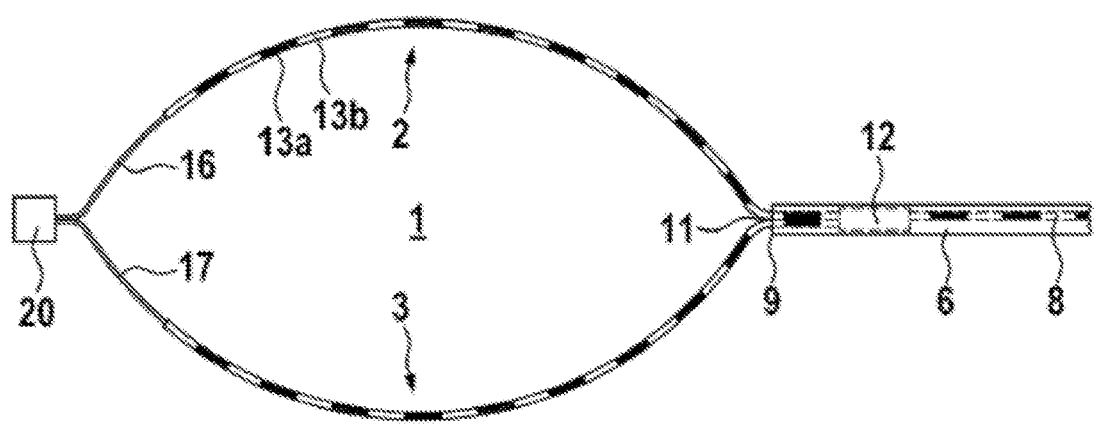
FIG. 5 shows a snare with a flat skid.

In FIG. 5, a flat skid 20 is shown. It may, for example, be rolled up to guide it through the catheter.

Figure 6:
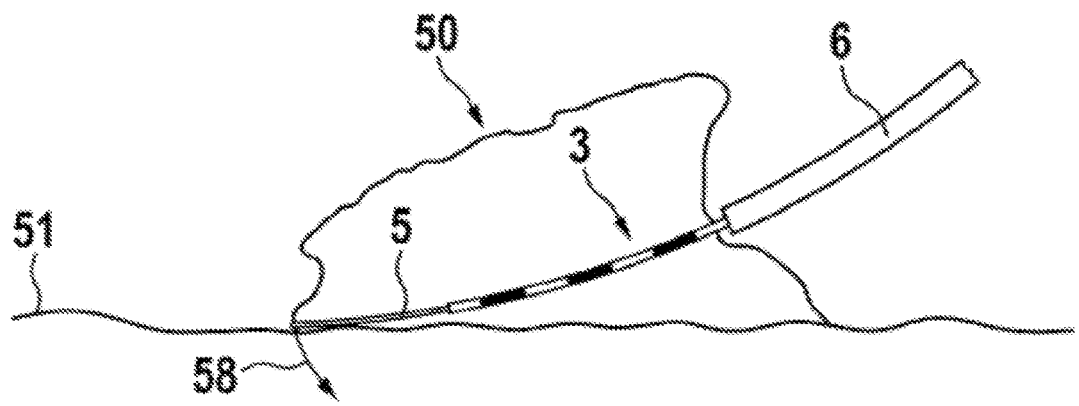
FIG. 6 shows the risk of penetrating of a cutting snare into an organ wall.

FIG. 6 shows, that cutting without skid bears the risk of an undesired penetration into the organ wall. A pathological tissue area 50 is enclosed by the snare.

Here, the second snare part is visible in the side view. Usually, the catheter 6 comes out of the middle of the hollow organ, such as the intestine, and thus lies at an angle with respect to the organ wall 51. In order to be able to remove the pathological area as close as possible to the organ wall, the snare must be pressed against the organ wall. This produces a force in the direction of penetration 58 towards the organ wall. Thus, the non-insulated region 5 of the snare can now penetrate in the direction 58 into the organ wall and damage it, resulting in the worst case in perforation of the organ.

Figure 7:
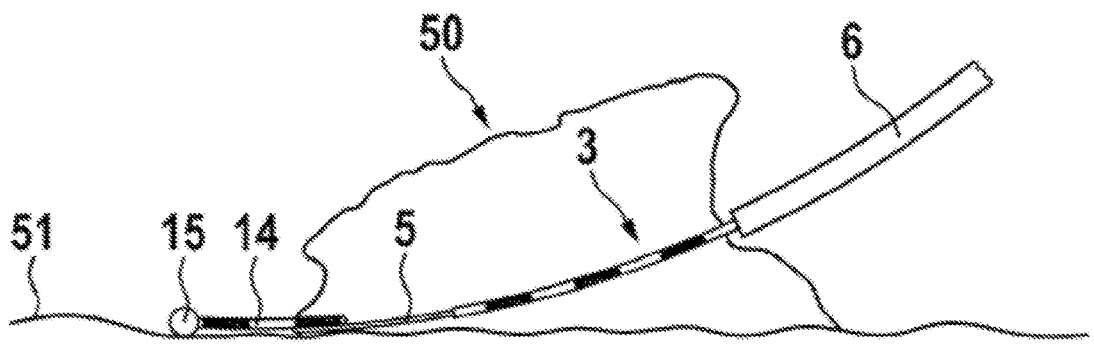
FIG. 7 shows the effect of a skid.

FIG. 7 shows, how penetration of the snare into the organ wall is avoided by means of a skid. Here, the skid 14 with its protection 15 rests on the organ wall and thus prevents penetration of the non-insulated region 5 into the organ wall. It is obvious that with a longer skid 14, a longer lever and thus a better protection against penetration of the non-insulated region 5 into the intestinal wall can be achieved. Likewise, the bearing surface on the organ wall 51 can be enlarged by a longer skid 14 and/or by a greater protection 15. Often, the surface of the organ wall itself is elastic and gives way at least slightly upon pressure by skid. This can be counteracted by increasing the bearing surface.

LIST OF REFERENCE NUMBERS 1 resection snare
2 first snare part
3 second snare part
5 non-insulated region
6 catheter
7 catheter tip snare tip
8 manipulation wire
9 distal end of the catheter
10 distal end of the resection snare
11 proximal end of the resection snare
12 connecting element
13a, 13b contrasting markings
14 skid
15 protection
16 first non-insulated region
17 second non-insulated region
18a, 18b skid
19 skid
20 flat skid
50 pathological tissue area
51 organ wall
58 penetration direction

The invention claimed is:

1. A resection snare comprising:
a first snare portion having a first electrical conductor, a first length, a first proximal end, and a first distal end, the first electrical conductor having a first insulation element electrically insulating said first electrical conductor at the first proximal end;
a second snare portion having a second electrical conductor, a second length, a second proximal end, and a second distal end, the second electrical conductor having a second insulation element electrically insulating said second electrical conductor at the second proximal end;
wherein at least one of the first and second electrical conductors includes a non-electrically insulated region at the corresponding first and second distal ends;
a catheter containing and configured to guide a manipulation wire therein,
wherein
a) the first and second proximal ends are electrically connected with or merging at a location of said manipulation wire and
b) the first and second snare portions are electrically connected to one another at a point of electrical connection opposite to said location
to close the first and second electrical conductors into an electrically-conducting snare loop;
and
wherein the resection snare includes at least one electrically-insulated HF-surgically inactive skid formed by at least one of the first and second distal ends extending outside said snare loop, said electrically-insulated HF-surgically inactive skid configured to be brought in contact with an organ wall during operation of the resection snare to support the snare loop against the organ wall while preventing the snare loop from penetrating into the organ wall.

2. The resection snare according to claim 1, wherein said non-electrically-insulated region of the at least one of the first and second electrical conductors has a length in a range from 10 mm to 30 mm.

3. The resection snare according to claim 2, wherein said snare loop is configured to be moveable in and out of the catheter with the manipulation wire.

4. The resection snare according to claim 1, wherein said at least one electrically-insulated HF surgically inactive skid is present on an opposite side of said non-electrically-insulated region as seen from a snare center.

5. The resection snare according to claim 1, wherein at least one of the first and second snare portions includes at least one of (i) a resilient metallic braid and (ii) a resilient metallic wire, said metallic wire being round or flat.

6. The resection snare according to claim 1, wherein said at least one electrically-insulated HF surgically inactive skid is present on an opposite side of said non-electrically-insulated region as seen from a snare center.

7. The resection snare according to claim 6, wherein at least one of the first and second snare portions includes at least one of (i) a resilient metallic braid and (ii) a resilient metallic wire, said metallic wire being round or flat.

8. The resection snare according to claim 6, wherein said snare loop is configured to be moveable in and out of the catheter with the manipulation wire.

9. The resection snare according to claim 1, wherein the at least one electrically-insulated HF surgically inactive skid includes a portion of at least one of the first and second electrical conductors extending beyond the point of electrical connection of the first and second electrical conductors such that a free end of said at least one electrically-insulated HF surgically inactive skid corresponding to one of the first and second distal ends is outside of the snare loop.

10. The resection snare according to claim 9, further comprising a protection element attached to a free end of the at least one electrically-insulated HF surgically inactive skid.

11. The resection snare according to claim 1, wherein at least one of the first and second snare portions includes at least one of (i) a resilient metallic braid and (ii) a resilient metallic wire, said metallic wire being round or flat.

12. The resection snare according to claim 1,
wherein the at least one electrically-insulated HF surgically inactive skid includes first and second electrically-insulated HF surgically inactive skids, the first electrically-insulated HF surgically inactive skid being formed by a portion of the first electrical conductor extending beyond the point of electrical connection of the first and second electrical conductors, the second electrically-insulated HF surgically inactive skid formed by a portion of the second electrical conductor extending beyond said point.

13. The resection snare according to claim 12, further comprising
a first protection element at a free end of the first electrically-insulated HF surgically inactive skid, and
a second protection element at a free end of the second electrically-insulated HF surgically inactive skid.

* * * * *